United States Patent
King et al.

(10) Patent No.: US 10,590,919 B2
(45) Date of Patent: Mar. 17, 2020

(54) GROUND BASED SYSTEMS AND METHODS FOR TESTING REACTION THRUSTERS

(71) Applicant: Aerojet Rocketdyne, Inc., Sacramento, CA (US)

(72) Inventors: David Q. King, Woodinville, WA (US); Peter Y. Peterson, Bothell, WA (US); Justin M. Pucci, Bothell, WA (US)

(73) Assignee: Aerojet Rocketdyne, Inc.

( * ) Notice: Subject to any disclaimer, the term of this patent is extended or adjusted under 35 U.S.C. 154(b) by 476 days.

(21) Appl. No.: 15/033,974

(22) PCT Filed: Apr. 7, 2014

(86) PCT No.: PCT/US2014/033133
§ 371 (c)(1),
(2) Date: May 3, 2016

(87) PCT Pub. No.: WO2015/065518
PCT Pub. Date: May 7, 2015

(65) Prior Publication Data
US 2016/0273523 A1   Sep. 22, 2016

Related U.S. Application Data

(60) Provisional application No. 61/899,842, filed on Nov. 4, 2013.

(51) Int. Cl.
*G01N 27/62* (2006.01)
*F03H 1/00* (2006.01)
(Continued)

(52) U.S. Cl.
CPC .............. *F03H 1/0075* (2013.01); *B64G 7/00* (2013.01); *F03H 1/00* (2013.01); *G01L 21/30* (2013.01);
(Continued)

(58) Field of Classification Search
CPC ........ G01L 21/30; G01N 27/62; G01N 27/64; H01J 41/00; H01J 41/02
(Continued)

(56) References Cited

U.S. PATENT DOCUMENTS

| | | | |
|---|---|---|---|
| 6,121,569 A * | 9/2000 | Miley | H05H 1/54 219/121.36 |
| 2002/0179858 A1 * | 12/2002 | Smith | G21F 5/10 250/493.1 |

(Continued)

OTHER PUBLICATIONS

Adam Boxberger, "Experimental Test Campaign of Gas-fed Steady State Applied-Field Magnetoplasmadynamic Thruster SX3", Oct. 6-10, 2013, The 33st International Electric Propulsion Conference, The George Washington University, USA, pp. 1-8.*
(Continued)

*Primary Examiner* — Raul J Rios Russo
(74) *Attorney, Agent, or Firm* — Carol Thustad-Farsyth; Fox Rothschild

(57) ABSTRACT

System (300, 400) and methods (500) for testing a reaction thruster (100) in a vacuum environment. The methods comprise: disposing the reaction thruster in a vacuum chamber which is at least partially connected to earth ground; removing at least one gas from the vacuum chamber to provide the vacuum environment; operating the reaction thruster so as to create a beam of electrons; and/or electrically isolating the electrons of the beam from at least one electrically conductive surface of the vacuum chamber. The electrical isolation can be achieved by applying an electrical bias voltage to the beam via an electrode. The electrode may comprise a conductive object disposed in the vacuum chamber and/or at least a portion of a vacuum chamber wall. In all cases, the electrode is electrically isolated from a portion of the vacuum chamber that is connected to ground.

20 Claims, 7 Drawing Sheets

(51) Int. Cl.
*B64G 7/00* (2006.01)
*G01L 21/30* (2006.01)
*G01N 27/64* (2006.01)
*H01J 41/00* (2006.01)
*H01J 41/02* (2006.01)

(52) U.S. Cl.
CPC ............. *G01N 27/62* (2013.01); *G01N 27/64* (2013.01); *H01J 41/00* (2013.01); *H01J 41/02* (2013.01); *B64G 2007/005* (2013.01)

(58) Field of Classification Search
USPC .................................................. 324/459–470
See application file for complete search history.

(56) References Cited

U.S. PATENT DOCUMENTS

| | | | | |
|---|---|---|---|---|
| 2003/0183783 | A1* | 10/2003 | Smith | G21F 5/10 250/493.1 |
| 2004/0139723 | A1* | 7/2004 | Parkin | F03H 99/00 60/203.1 |
| 2006/0261759 | A1* | 11/2006 | Chen | H05H 11/00 315/507 |
| 2008/0047256 | A1* | 2/2008 | Gallimore | H01J 27/022 60/202 |
| 2008/0067430 | A1* | 3/2008 | Hershkowitz | F03H 1/0025 250/492.3 |
| 2009/0058305 | A1* | 3/2009 | Hofer | B64G 1/405 315/111.91 |
| 2009/0229240 | A1* | 9/2009 | Goodfellow | B64G 1/401 60/202 |
| 2009/0250555 | A1* | 10/2009 | Adamo | B64G 1/443 244/172.7 |
| 2010/0151679 | A1* | 6/2010 | Gu | C25D 5/02 438/675 |
| 2011/0080093 | A1 | 4/2011 | Walton et al. | |
| 2011/0248179 | A1* | 10/2011 | Matesa, Jr. | H01J 27/04 250/396 ML |
| 2013/0026917 | A1 | 1/2013 | Walker et al. | |
| 2014/0306065 | A1* | 10/2014 | Palmer | F41A 1/04 244/171.1 |
| 2015/0128560 | A1* | 5/2015 | Conversano | F03H 1/0075 60/202 |
| 2016/0207642 | A1* | 7/2016 | Longmier | F03H 1/0093 |
| 2016/0299103 | A1* | 10/2016 | Saleh | H01J 33/00 |
| 2017/0158356 | A1* | 6/2017 | Palmer | F41F 1/00 |

OTHER PUBLICATIONS

Harmann, et al., "The ULAN Test Station and its Diagnostic Package for Thruster Characterization," IEPC-2007-119, Sep. 20, 2007, Presented at the 30th International Electric Propulsion Conference, Florence, Italy, Sep. 17-20, 2007.
International Search Report and Written Opinion dated Aug. 27, 2014 for PCT/US14/33133.

* cited by examiner

GROUND BASED SYSTEMS AND METHODS FOR TESTING REACTION THRUSTERS

CROSS REFERENCE TO RELATED APPLICATIONS

The present application claims benefit of International (PCT) Patent Application No. PCT/US2014/033133 filed on Apr. 7, 2014 and entitled "Ground Based Systems and Methods for Testing Reaction Thrusters", and U.S. Provisional Patent Application Ser. No. 61/899,842 filed on Nov. 4, 2013 and entitled "Ground Based Systems and Methods for Testing Reaction Thrusters". The contents of these two patent applications are incorporated herein by reference in their entirety.

BACKGROUND

Statement of the Technical Field

The disclosure relates to reaction thrusters (e.g., Hall or ion thrusters). More particularly, the disclosure concerns systems and methods for ground based testing of reaction thrusters intended for use in low density and pressure environments (e.g., outer space, or an altitude greater than 122 km).

Description of the Related Art

There are many reaction thrusters known in the art, such as ion thrusters. Ion thrusters are generally used to propel a craft by accelerating ions. A Hall Effect type ion thruster comprises an electrode inside of a discharge channel (anode), a downstream cathode to provide electrons, and an applied mostly "radial" magnetic field topology in the discharge channel. The magnetic field topology is established by a magnetic circuit and a ferromagnetic structure. The magnetic circuit is composed of either electromagnetic coils or permanent magnets. The ferromagnetic structure behaves as flux channels for the magnetic fields generated by the field sources. An axial electric field is developed between the anode, which also can function as the neutral propellant distribution system in the discharge channel, and the electron emission source (cathode). Electrons emitted from the cathode are attracted towards the anode due to the potential gradient applied between the cathode and anode. The electrons that are accelerated towards the anode enter the discharge channel where they begin to experience an azimuthal ExB drift, creating what is referred to as the Hall current. The Hall current effectively impedes the majority of the axial electron motion towards the anode. The Hall current region forms what is described as a "virtual cathode". The trapped electrons gyrate azimuthally around the discharge channel until they are either lost to the walls or anode, recombined, or involved in an ionization collision with neutral propellant particles flowed from upstream of the Hall current region. The ionized propellant gas then accelerates through the potential gradient maintained by the Hall current. The accelerated ion beam pulls additional electrons from the cathode into the ion beam to form a quasi-neutral propulsive plasma.

In some scenarios, ion thrusters are used to control the orientation and position of objects orbiting the earth (e.g., satellites). Accordingly, ion thrusters are designed to operate in a low density and pressure environment. Prior to deployment in such an environment, operation of the ion thruster is tested in a test environment. The test environment is intended to mimic the low density and pressure environment. In this regard, the test environment is created using a vacuum chamber (i.e., an enclosure from which air and other gases are removed by one or more vacuum pumps). The vacuum chamber is often formed of a conductive material (e.g., steel) which is typically connected to earth ground.

SUMMARY

The disclosure concerns implementing systems and methods for testing a reaction thruster (e.g., an ion thruster) in a vacuum chamber environment. The methods involve: disposing the reaction thruster in a vacuum chamber which is at least partially connected to earth ground and at least partially formed of a conductive material; removing at least one gas from the vacuum chamber to provide the vacuum environment; operating the reaction thruster so as to create a beam of electrons; and/or electrically isolating the electrons and/or ions of the beam from at least one electrically conductive surface of the vacuum chamber.

In some scenarios, the electrical isolation is achieved by (1) applying an electrical bias voltage to the beam, (2) disposing a dielectric or floating material adjacent to the electrically conductive surface of the vacuum chamber, and/or (3) isolating the ion thruster and the beam from the vacuum chamber and other equipment disposed in the vacuum chamber.

With regard to option (1), the electrical bias voltage is applied to the beam using an electrode disposed inside and electrically isolated from the vacuum chamber. The electrode comprises a conductive object (e.g., a plate or a porous screen) located downstream from the reaction thruster. A constant bias voltage is applied to the electrode during operation of the reaction thruster. The applied bias voltage drives the ion and electron beam average plasma potential in the direction of the applied bias voltage. With sufficient biasing, the beam is preferentially shifted such that it does not interact with the vacuum chamber, thereby stimulating a more outer space like environment. Alternatively, the value of the voltage applied to the electrode is dynamically varied during operation of the ion thruster. The dynamic variation is performed based one or more parameters. The parameters include, but are not limited to, a density of neutral gas within the vacuum chamber, a voltage of the cathode of the reaction thruster to the vacuum chamber, a value of the current in the plasma flowing from the reaction thruster, and/or an amount of current collected at electrode.

In other scenarios, the electrical isolation is achieved by applying a voltage to a downstream end of the vacuum chamber such that the downstream end has a different electrical potential relative to the beam of ions and electrons. Notably, the downstream end of the vacuum chamber is electrically isolated from an upstream end of the vacuum chamber which is connected to earth ground. The terms "upstream" and "downstream" are used herein to describe directions with respect to movement of ions in a channel of a reaction thruster.

With regard to options (2) and (3), the isolation of the ion thruster beam is achieved by the placement of at least one dielectric, or floating, material in the vacuum chamber. In this case, electrons from the ion thruster are impeded from potential conductive paths that are not present in low density and pressure environment.

BRIEF DESCRIPTION OF THE DRAWINGS

Embodiments will be described with reference to the following drawing figures, in which like numerals represent like items throughout the figures, and in which.

DETAILED DESCRIPTION

The term "plasma", as used herein, refers to an ionized gas consisting of neutral atoms, ions and free electrons.

The term "electron", as used herein, refers to a stable subatomic particle with a charge of negative electricity (e.g., −1).

The term "ion", as used herein, refers to an atom or a group of atoms that has one or more electrons removed from the atoms outer electron shells, giving it a net positive charge.

The term "beam", as used herein, refers to neutral atoms, ions and electrons emitted from a reaction thruster.

The term "outer space", as used herein, refers to a region of space immediately beyond the earth's atmosphere.

Figure 1:
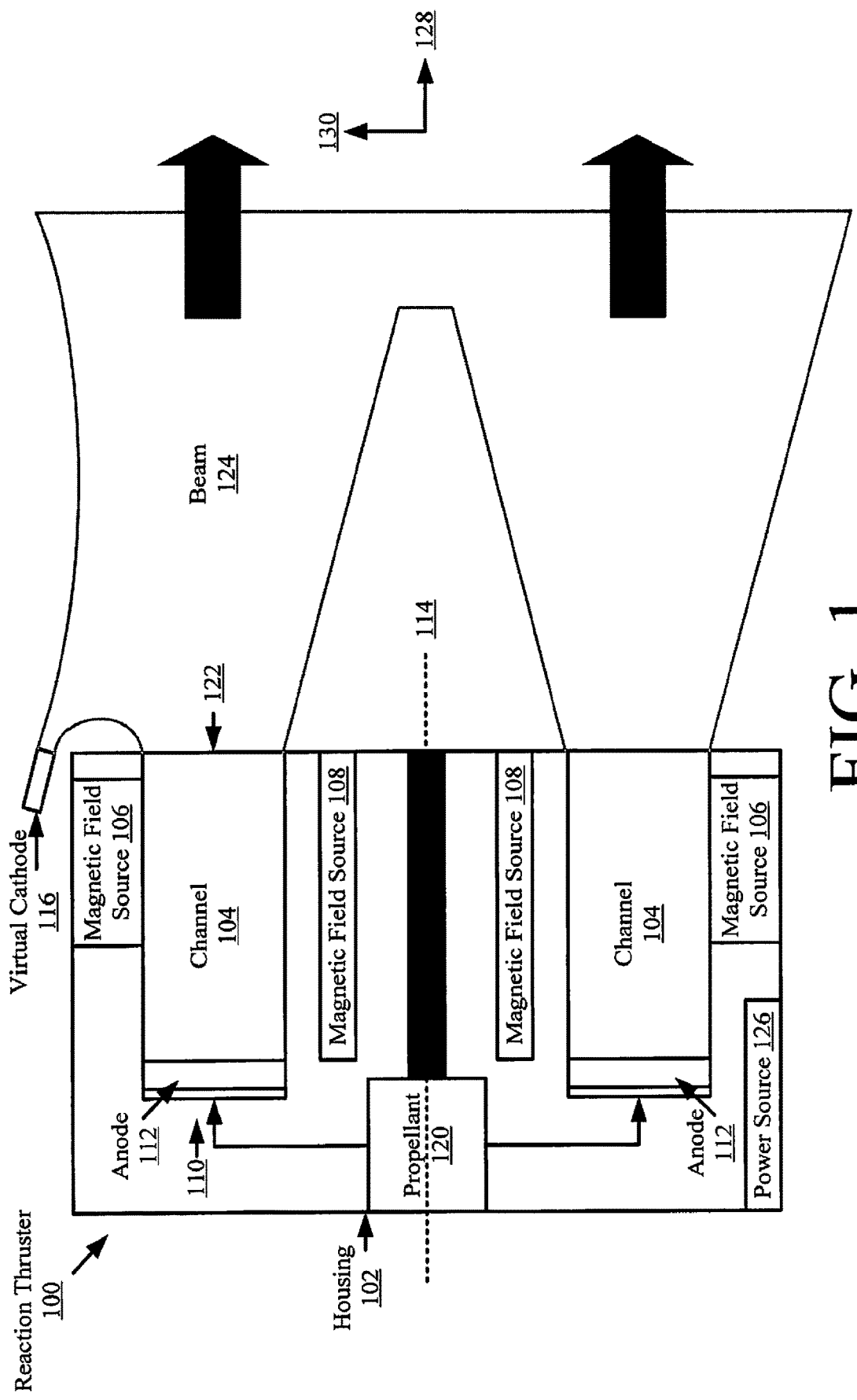
FIG. 1 is a schematic illustration of an exemplary reaction thruster.

Referring now to FIG. 1, there is provided a schematic illustration of an exemplary reaction thruster 100. More specifically, a cross-sectional view of a Hall Effect type of ion thruster is provided in FIG. 1. A Hall Effect type of ion thruster is configured to accelerate propellant by an electric field so as to produce thrust. Embodiments of the present invention are not limited to the Hall Effect type of ion thrusters. Accordingly, the reaction thruster 100 can alternatively include any other type of ion thruster or plasma based reaction thruster.

In general, reaction thruster 100 is configured for use on a satellite or other spacecraft to assist in adjusting its position when in orbit around the earth, to move it into the desired orbit, or for propelling it during long missions (e.g., inter-planetary missions). In this regard, the reaction thruster 100 comprises various thruster components 104-116, 120-126 disposed within a housing 102 which can be securely coupled to the satellite or other spacecraft. The housing 102 may be at least partially formed of an electrically conductive material. The thruster components include a power source 126, a propellant 120, a channel 104 (e.g., an annular channel) and magnetic field sources 106, 108. The power source 126 may include, but is not limited to, a battery, a fuel cell, and/or a solar cell. The propellant 120 can include, but is not limited to, xenon, krypton, argon, bismuth, iodine, magnesium and/or zinc.

During operation, the reaction thruster 100 uses an electric potential to accelerate ions up to high speeds (e.g., 20 kilometers per second). The electric potential is maintained between a cylindrical anode 112 and a virtual cathode 116 formed by the Hall current. In some scenarios, an electric potential between 100 Volts and 1000 Volts is applied between the anode 112 and cathode 116. Embodiments are not limited to this exemplary voltage range.

Thereafter, the propellant 120 is introduced into the channel 104 through passages (not shown) formed in the anode 112. The passages of the anode 112 act as a gas distributor. The anode 112 is located at a closed end 110 of the channel 104. The channel 104 extends circumferentially around an axis 114 of the reaction thruster 100 and also extends in an axial direction from the closed end 110 to an open end 122. The cathode 116 is located outside of the channel 104 near the open end 122.

The magnetic field sources 106, 108 apply a magnetic field in a mostly radial direction across the channel 104. In some scenarios, the radial magnetic field is of at least a hundred gauss (e.g., about 100-500 G, 0.01-0.05 T). The electric and magnetic fields cause electrons emitted from the cathode 116 to move circumferentially around the channel 104. Some of these electrons pass into the channel 104 towards the anode 112. The radial magnetic field deflects the electrons in a circumferential direction so that they move in a helical trajectory As the propellant 120 diffuses into the channel 104 of the reaction thruster 100, atoms thereof collide with the high energy circulating electrons thereby causing ionization. As noted above, an ion is an atom or a group of atoms that has one or more electrons removed from the atoms outer electron shells, giving it a net positive charge. As such, the propellant ions (e.g., xenon ions) typically have a charge of +1, +2, and/or +3.

The positively charged propellant ions are then attracted towards the virtual cathode 116 formed by the Hall current. In this regard, the propellant ions are expelled at a high velocity from the open end 122 of the channel 104, thereby producing thrust. Upon exiting the channel 104, the propellant ions attract electrons so as to form a beam 124 of ions and electrons.

Notably, the flow of the ionized propellant 120 has three constituent parts: ions; electrons; and neutral particles. These constituent parts have different behaviors. For example, the electrons have a much smaller mass as compared to the ions. Accordingly, the electrons are affected by the radial magnetic field, and therefore move in a radial direction 130 with respect to the channel 104. Also, the electrons move with an electric field when located a certain distance (e.g., 20 centimeters) from the reaction thruster 100. In this regard, the electrons travel wherever the electrical field sends them (i.e., the electrons can flow away from the thruster in an axial direction 128 as well as any radial directions 130). Thus, the ions have a much greater mass as compared to the electrons. As such, the ions are largely unaffected by the radial magnetic field, and therefore move primarily in the axial direction 128 away from the reaction thruster 100. There is some expansion or relative dispersion of the ions in the radial direction 130. This expansion or relative dispersion is influenced by the electrons since the ions are electrically attracted to the electrons.

As noted above, the reaction thruster 100 can be used to control the orientation and position of objects orbiting the earth (e.g., satellites), as well as the main or secondary propulsion system for objects (e.g., a spacecraft) traveling in interplanetary space. Accordingly, the reaction thruster 100 is designed to operate in a relatively low density and pressure environment. Prior to deployment in the relatively low density and pressure environment, operation of the reaction thruster 100 is tested in a terrestrial test environment (e.g., a vacuum chamber environment). The terrestrial test environment is intended to mimic the low density and pressure environment of outer space. In this regard, the test environment is created using a test system. An exemplary test system is shown in FIG. 2.

Figure 2:
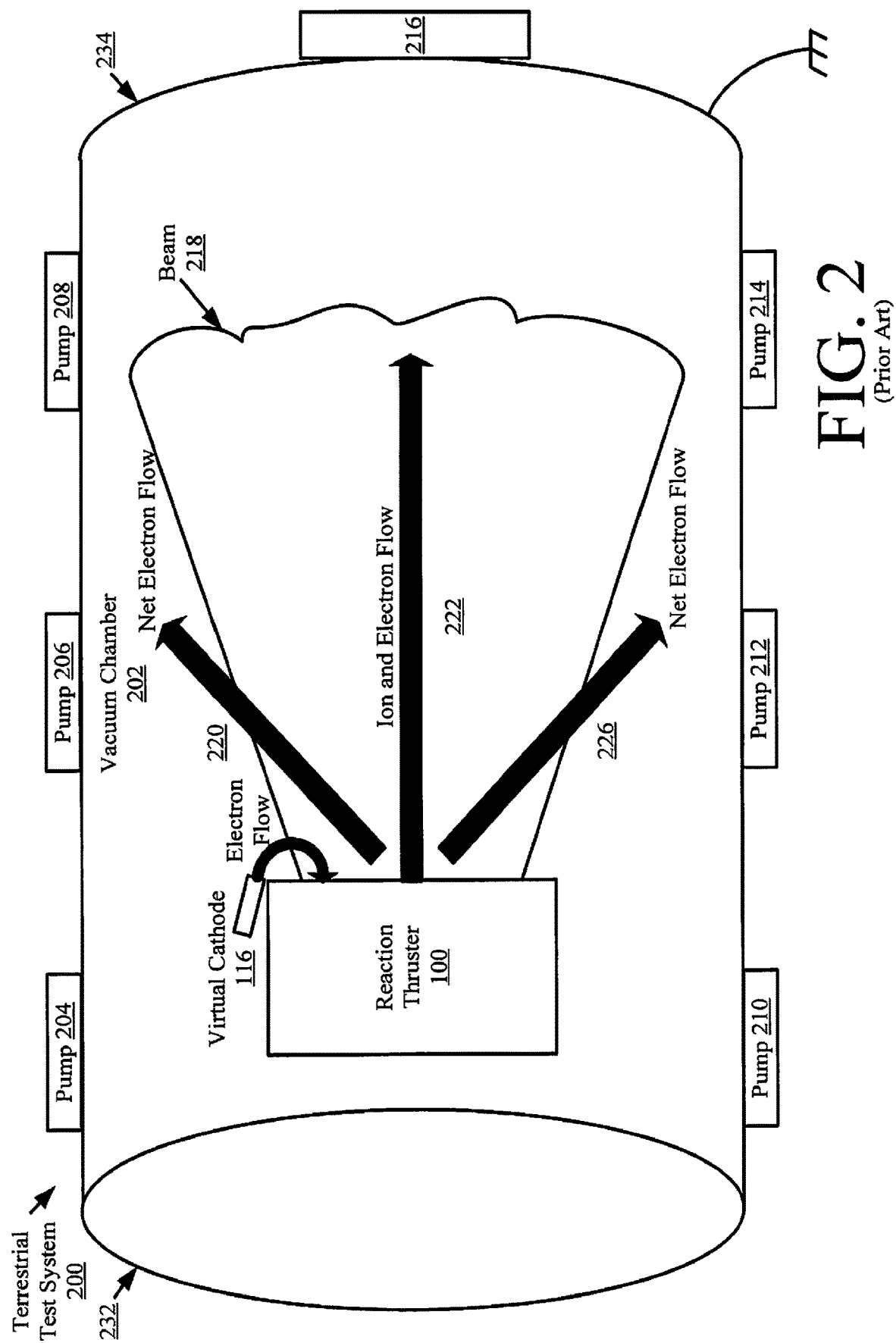
FIG. 2 is a schematic illustration of an exemplary test system.

Referring now to FIG. 2, there is provided a schematic illustration of an exemplary terrestrial test system 200 for reaction thrusters (e.g., reaction thruster 100 of FIG. 1). Test system 200 is generally configured to provide a low density and pressure environment for testing operations of the reaction thruster 100 (e.g., a Hall Effect type of ion thruster). In this regard, the terrestrial test system 200 comprises a vacuum chamber 202 and at least one vacuum pump ("pump") 204-216. Vacuum chamber 202 is an enclosure from which air and other gases are removed by the vacuum pump(s) 204-216. This results in a low pressure environment within the vacuum chamber 202 ("vacuum environment"). The vacuum environment allows one to analyze the operations of the reaction thruster 100 in a simulation of a relatively low density and pressure environment in which it is intended to operate.

The vacuum chamber 202 is formed of an electrically conductive material. The electrically conductive material can include, but is not limited to, stainless steel, aluminum, mild steel, and/or brass. The vacuum chamber 202 has a generally cylindrical shape with closed ends 232, 234. In other scenarios, the vacuum chamber 202 may have a shape other than a cylindrical shape, such as a spherical shape. Typically, a terrestrial vacuum chamber 202 is connected to earth ground as shown in FIG. 2, and therefore has a voltage of approximately 0 Volts.

Figure 3:
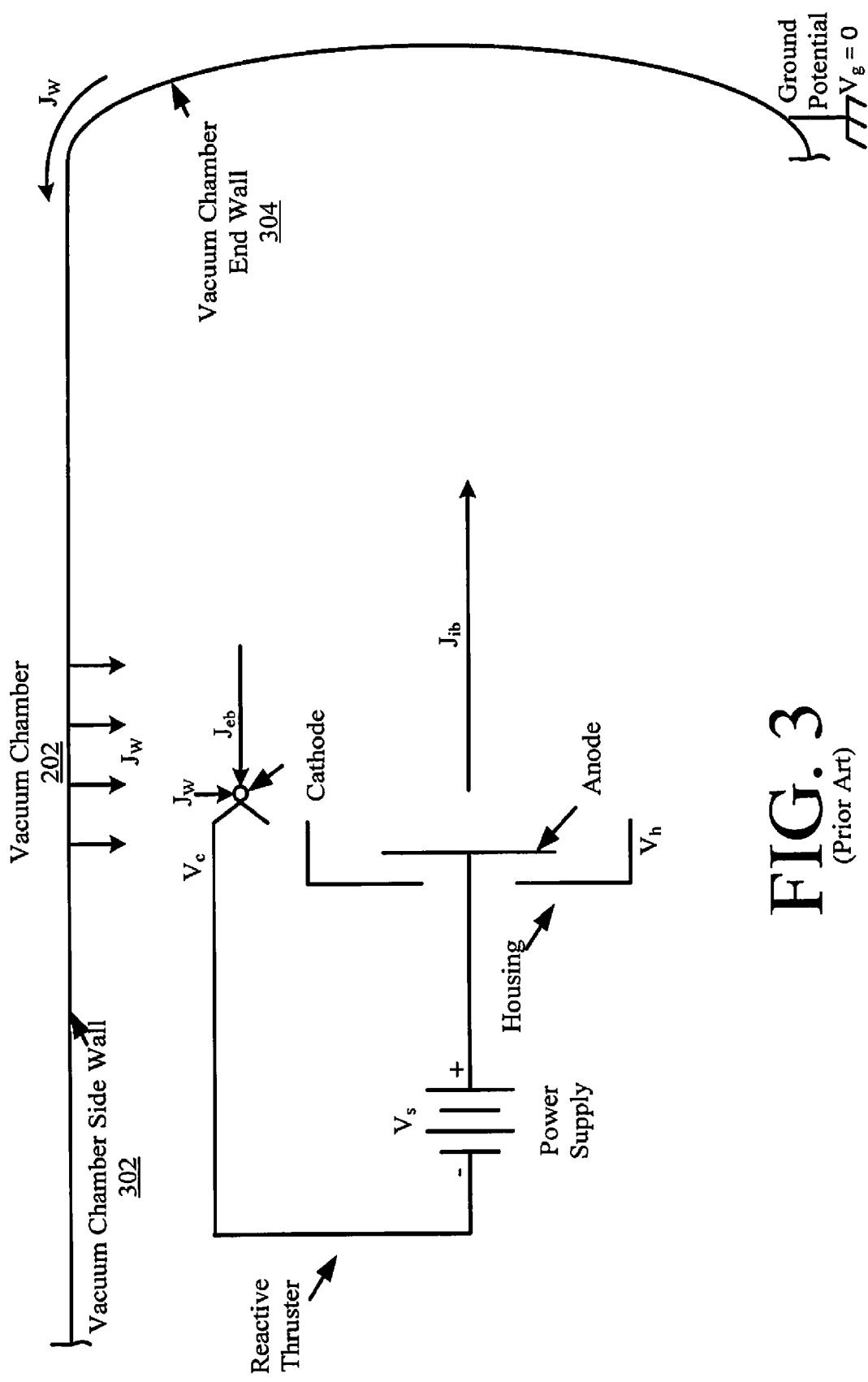
FIG. 3 is a schematic illustration that is useful for understanding an equilibrium condition for a reaction thruster operating in the vacuum chamber of FIG. 2.

Referring now to FIG. 3, there is provided a schematic illustration that is useful for understanding an equilibrium condition for a reaction thruster (e.g., reaction thruster 100 of FIG. 1) operating in the terrestrial vacuum chamber 202 conductive material(s). Only a portion of the vacuum chamber 202 is shown in FIG. 3. The reaction thruster is shown without detail, including only a cathode (e.g., cathode 116 of FIG. 1), anode (e.g., anode 112 of FIG. 1) and housing (e.g., hosing 102 of FIG. 1). In this case representing a typical terrestrial test environment, beam potentials adjust to an equilibrium value determined by a combination of ion and electron currents reaching the walls 302 of the vacuum chamber. These currents are driven by different phenomena. Dependent on a background pressure, ions may not collide with another particle. In this case, the ions travel in straight lines. Because the ions have been given substantial momentum and energy, they are only slightly affected by varying potentials in the beam. Electrons being 10,000 times lighter have a much less directed momentum and are caused to follow different paths than ions, a path defined by beam potentials. In this way, ions travel axially away from the reactive thruster or accelerator and diverge somewhat radially. Electrons are free to follow the path of least resistance and will eventually balance the collected ion current be it in the beam and/or the conductive chamber walls.

An electrical boundary layer, called a sheath, is developed at the interface of the plasma and any surface inside the vacuum chamber 202. Along the vacuum chamber side wall 302, because of low ion flux, the sheath potential may be positive with respect to the vacuum chamber (e.g., up to +10 Volts). Along the vacuum chamber end wall 304, where this is high ion flux, the sheath potential is small (e.g., ≤+1 Volt). This difference in voltage from the end wall 304 to the sidewall 302 enables a circulating current in the beam and the wall affecting the beam potential equilibrium. The positive potential on the side wall 302 attracts beam electrons which are absorbed and become a current flowing in the wall. The majority of ions reach the end wall 304. In total, the number of ions reaching the end wall 304 must by conservation of charge be equal to the number of electrons absorbed on the wall 302. However, because the vacuum chamber walls 302, 304 are conductive, opposite charges may arrive at different locations and neutralize through current flowing in the walls 302, 304. A portion of electrons will find a path of least resistance by absorbing on the grounded vacuum chamber side wall as well as any conductive surfaces in the vacuum chamber that is in electrical contact with the vacuum chamber. These electrons travel along the ground conductive paths 302 to the end wall 304 where they are neutralized by net ion absorption. This corresponds to the following mathematical Equation (1).

$$J_W = J_{ib} - J_{eb} \quad (1)$$

where $J_W$ is a ground surface current (e.g., a wall current), $J_{ib}$ is an ion beam current, and $J_{eb}$ is a neutralizing electron current.

The equilibrium beam potentials are such that the cathode potential $V_c$ is negative relative to the vacuum chamber, typically −25 to −10 Volts. Electrons leave the cathode and mode towards more positive potentials, including the thruster body and the vacuum chamber walls. Note that the direction of electron velocity is opposite the current flow owing to the negative charge of electrons.

As noted above, the test system 200 is able to provide a vacuum environment for terrestrial testing of reaction thrusters. The nature of the terrestrial vacuum environments relay on vacuum pumps to remove atmospheric gasses, expelled propellant gas, and any outgassed gasses from the vacuum chamber and associated equipment to simulate outer space vacuum levels for assessing the operation of the reaction thruster. The vacuum pumps operate by trapping and/or removing the excess gasses that enter and/or come into contact with the vacuum pumps. For example, during the operation of a reaction thruster, some gas flowing out of the reaction thruster 100 may not be effectively or immediately removed by the pumps 204-216 during a testing process. This gas may reflect off surfaces of the pumps 204-216, thereby increasing the density of neutral gas within the vacuum chamber 202. Also, unionized gas may escape the reaction thruster 100 in the vacuum environment and the space environment.

In the terrestrial vacuum environment, the density of gas may be 10-1000 times larger in the terrestrial vacuum environment as compared to that in the outer space environment. The higher density of gas results in a higher pressure of neutral gas within the terrestrial vacuum chamber 202. This higher pressure of neutral gas contributes to the conductivity of the beam 124. In this regard, it should be understood that the neutral gas is ionized by charge exchange with the ion beam 124, and therefore the conductive plasma is dispersed more widely within the terrestrial vacuum environment as compared to that within the outer space environment. The conductive plasma has a distribution of voltage. For example, the beam may have a voltage of −25 Volts near the cathode and +15 to +20 Volts in its center area. The voltage distribution relates to the flow of electrons and pressures acting on the electrons.

Additionally, the terrestrial conductive vacuum chamber 202 provides an electrical path that is not present in space based applications. As such, the vacuum chamber 202 may short out the natural potential difference within the beam 124 of the reaction thruster 100 being tested therein. The natural potential of the beam 124 is a result of the forces on the electrons and ions. As noted above, the electrons beyond a certain distance from the thruster (e.g., 20 centimeters) move with the electric field (i.e., the forces on the electrons, such as the pressure created by the ionized gas). In the terrestrial conductive vacuum environment, the electric field connects with the electrically conductive internal surfaces of the vacuum chamber 202. These electrically conductive internal surfaces include, but are not limited to, inner surfaces of the vacuum chamber walls defining its geometric shape. Consequently, the electrons are attracted to these electrically conductive surfaces, and therefore travel in unintended radial paths to the vacuum chamber walls, as shown by arrows 220 and 226. In effect, the electrons collect on the vacuum chamber walls in the radial direction from the reaction thruster 100. The result is that the equipotential of the vacuum chamber 202 becomes a path of least resistance for electron and ion flow which is not present in the space environment, thereby causing an electrical interference with the natural evolution of the beam 124. Because the plasma is distributed more widely in the terrestrial vacuum environment and the vacuum chamber disturbs the natural electric potentials of the beam 124, operation of the reaction thruster 100 is affected in the ground test as compared to that in space flight.

The effects of the test system 200 explained above increase with thruster power level. For example, in some scenarios, the reaction thruster 100 is a 4.5 kW system with a 300 Volt discharge and a 15 Amp current running between the primary electrodes and the thruster. From the discharge, approximately 12 Amperes of ions are created from the neutral propellant 120 injected into the channel 104. Therefore, there are 12 Amperes of electrons moving away from the reaction thruster 100. When the ions absorb electrons, they become neutral particles. Thereafter, the neutral particles are pumped out of the vacuum chamber 202 via the vacuum pumps 204-216. In this regard, the pressure of gas within the vacuum chamber 202 is maintained $6 \times 10^{-6}$ Torr. Even at the pressure of $6 \times 10^{-6}$ Torr, the gas density affecting the reaction thruster 100 is 100 times larger than exists in the space environment.

Some applications of electric propulsion for spacecraft require power levels to reach 50 kW or more. Since propellant flow rate generally increases with power, the ability to maintain a low vacuum level at 50 kW becomes prohibitively expensive to implement using certain terrestrial testing techniques. The expense is compounded by the fact that the operational life of a reaction thruster, which must undergo endurance testing, is desired to be 20,000 hours or more.

The disclosure depicts an approach to test reaction thrusters in a terrestrial test facility without the undesirable effects caused by conventional test systems (e.g., test system 200 of FIG. 2). Exemplary embodiments of a test system implemented by the terrestrial test facility of the present invention will now be described in relation to FIGS. 4-6.

Figure 4:
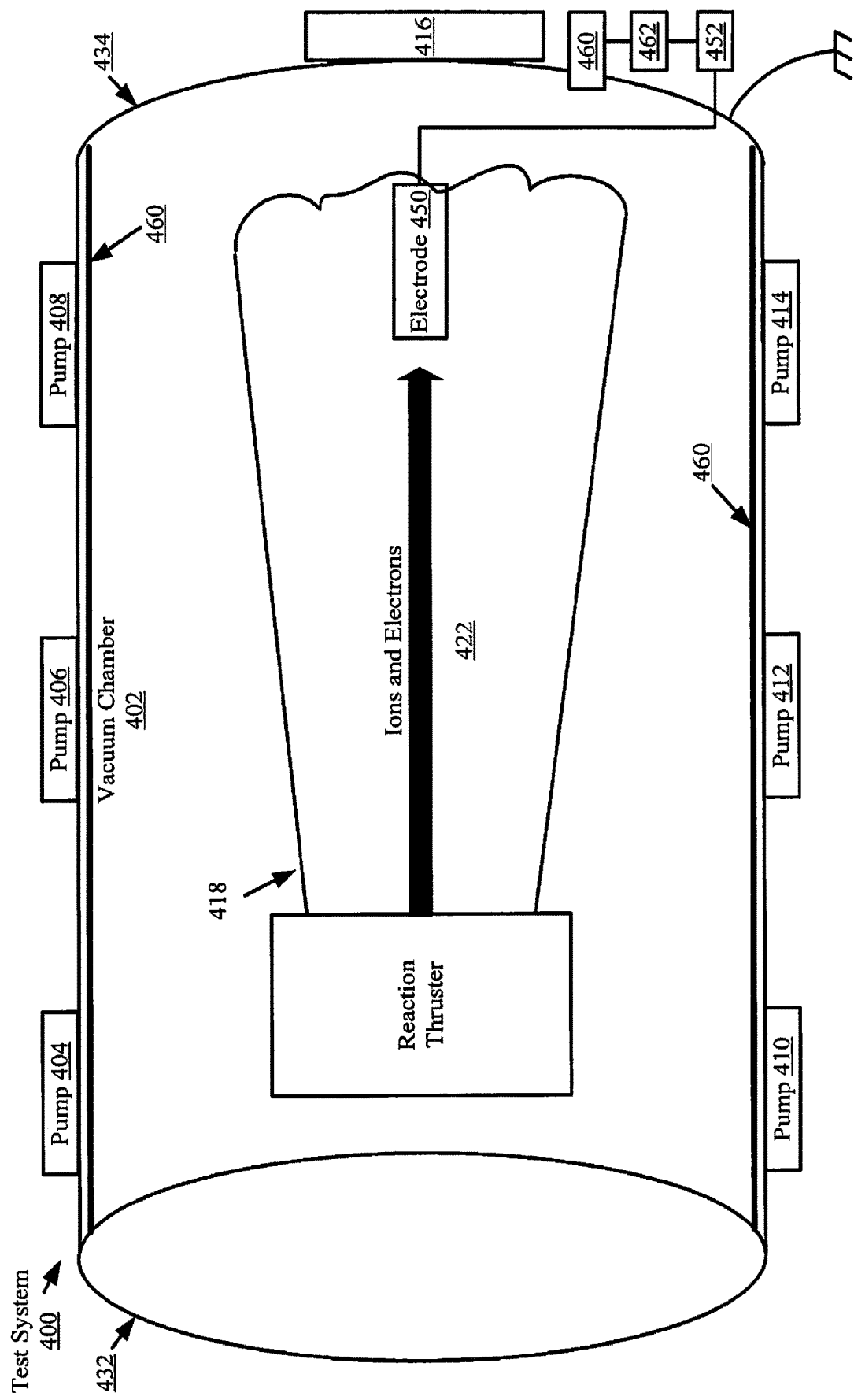
FIG. 4 is a schematic illustration of an exemplary test system.

Referring now to FIG. 4, there is provided a schematic illustration of an exemplary test system 400. Test system 400 is generally configured to provide a low density and pressure environment for testing operations of a reaction thruster (e.g., ion thruster 100 of FIG. 1). In this regard, test system 400 comprises a vacuum chamber 402 and at least one vacuum pump 404-416. Vacuum components 402-416 are the same as or similar to the corresponding vacuum components 202-216 of FIG. 2. As such, the description provided above in relation to vacuum components 202-216 is sufficient for understanding vacuum components 404-416 of test system 400.

Test system 400 is further configured to provide a novel means to test reaction thrusters without the undesirable effects caused by conventional test systems (e.g., test system 200 of FIG. 2). In this regard, test system 400 comprises a means to electrically isolate electrons in a beam from the electrically conductive walls of a vacuum chamber 402, the electrically conductive surfaces of the reaction thruster, and any other grounded equipment disposed in the vacuum chamber. This electrical isolation is achieved by: (1) optionally providing a dielectric or floating material 460 on or adjacent to one or more surfaces of the vacuum chamber walls so as to at least partially eliminate the path of least resistance provided thereby; (2) applying an electrical bias voltage to the plasma beam which causes the electrons to travel in the same general axial downstream direction as the ions, as shown by arrow 422; and/or (3) isolating the reaction thruster and the beam from the vacuum chamber and other equipment disposed in the vacuum chamber.

With respect to (2), the downstream end of the vacuum chamber 402 is made to have a more positive potential relative to the beam of electrons and ions. In this regard, the electrical bias voltage is applied to the beam 418 via at least one electrode 450 so as to bias the beam 418 positive with respect to the vacuum chamber walls. As shown in FIG. 4, electrode 450 is located within the most downstream portion of the beam 418. Embodiments of the present invention are not limited in this regard. The electrode(s) can be disposed at any location within a downstream portion of the vacuum chamber. For example, electrode 450 may alternatively be located adjacent to the reaction thruster or offset from a central axis (e.g., axis 114 of FIG. 1) of the reaction thruster.

In some scenarios, electrode 450 comprises at least one conductive plate or other object (e.g., a cone, sphere or rod) which is electrically separated from all of the vacuum chamber walls and is electrically connected to the power supply 452. The electrode 450 can also serve as the beam dump for the accelerated beam ions. Electric power is supplied to electrode 450 by the power supply 452. A positive voltage is applied to the electrode 450 relative to the vacuum chamber 402. For example, a positive bias of up to hundreds of Volts is applied to the electrode 450. The positive bias of up to hundreds of Volts value is selected to be sufficient for collecting a current equivalent to the ion beam current. Consequently, electrons are (1) drawn towards the positively biased electrode, rather than moving radially to the vacuum chamber walls or backwards towards the reaction thruster, and (2) electrons that move to the vacuum chamber walls are reflected therefrom.

In some scenarios, a constant positive voltage is applied the electrode 450. In other scenarios, the value of the voltage applied to the electrode 450 is dynamically varied during a testing process. Accordingly, test system 400 may further comprise one or more measurement devices 460 (e.g., a gauge) and a controller 462. The controller 462 is configured to: receive measurement values from the measurement device(s) 460; analyze the measurement values to determine whether a voltage level should be modified; and cause the power supply 452 to change the value of the voltage being supplied thereby to the electrode 450. The controller 462 can include hardware (e.g., an electronic circuit) and/or software configured to perform the above listed functions.

The dynamic variation of the voltage level may be based one or more parameters. The parameters may include, but are not limited to, a density of neutral gas within the vacuum chamber, a pressure of the neutral gas within the vacuum chamber, a voltage of the cathode of the reaction thruster to the terrestrial vacuum chamber or the plasma potential of the thruster beam, a value of the current in the plasma flowing from the reaction thruster, and/or an amount of current collected at electrode 450.

As noted above, the electrode 450 comprises one or more objects disposed within the vacuum chamber 402. Embodiments of the present invention are not limited to this particular architecture of the electrode. For example, the electrode can be formed to alternatively or additionally comprise at least a portion of the vacuum chamber (e.g., more than, less than, or equal to 50% of the vacuum chamber). An example of this electrode architecture is schematically illustrated in FIG. 5.

Figure 5:
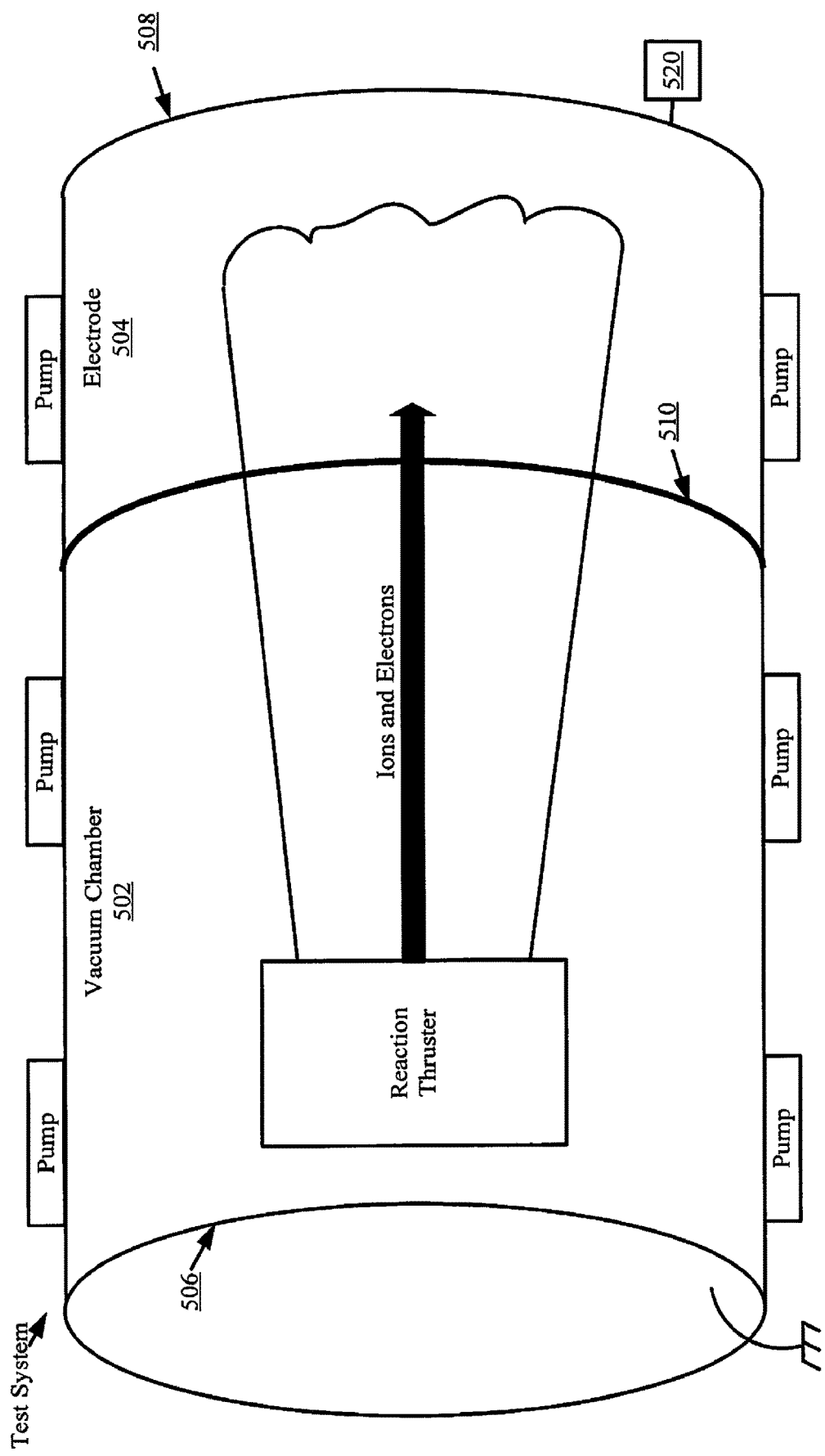
FIG. 5 is a schematic illustration of another exemplary test system.

As shown in FIG. 5, an electrode 504 comprises a portion 508 of the vacuum chamber 502. In this case, a first portion 506 of the vacuum chamber 502 is connected to ground, while the second portion 508 of the vacuum chamber 502 is connected to a power source 520. A dielectric material 510 is disposed between the two portions 506, 508 so as to electrically isolate them from each other.

Figure 6:
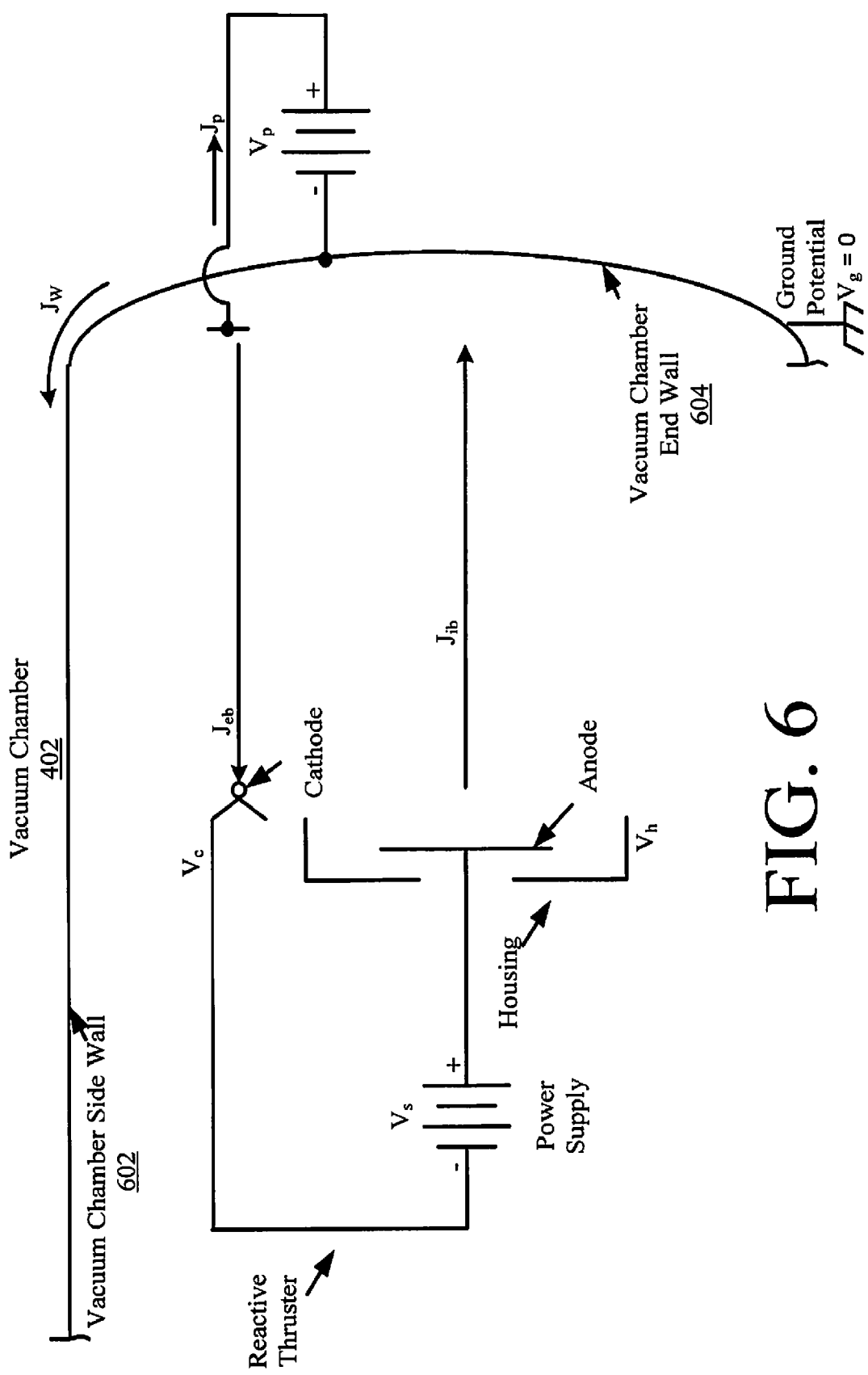
FIG. 6 is a schematic illustration that is useful for understanding how the beam potentials are altered by applying an electrical bias voltage thereto.

Referring now to FIG. 6, there is provided a schematic illustration that is useful for understanding how the beam potentials are altered by applying an electrical bias voltage $V_p$ (e.g., 0 Volt<$V_p$> hundreds of Volts) thereto. Stated differently, the beam potentials are altered by causing beam electrons to be attracted to a location downstream of the reaction thruster (e.g., reaction thruster 100 of FIG. 1) rather than the vacuum walls 602, 604. An object (e.g., electrode 450 of FIG. 4) is placed in a downstream location and biased by a power supply (e.g., power supply 452 of FIG. 4) sufficient to attract an electron current $J_{eb}$ approximately the same as the ion beam current $J_{ib}$. In this way, electrons are caused to flow primarily in the downstream direction.

Another aspect of this biasing is that the cathode potential $V_c$ is raised to a positive voltage above the vacuum chamber ground voltage ($V_g$). Cathode electrons are repelled by more negative potentials and hence are prohibited from reaching the side walls 602, 604. In this way, biasing the beam electrically simulates the space environment. This corresponds to mathematical Equations (2)-(4).

$$J_{ib}=J_{eb} \quad (2)$$

$$J_W=0 \quad (3)$$

$$J_p \approx J_{eb} \quad (4)$$

where $J_p$ is the bias current.

Figure 7:
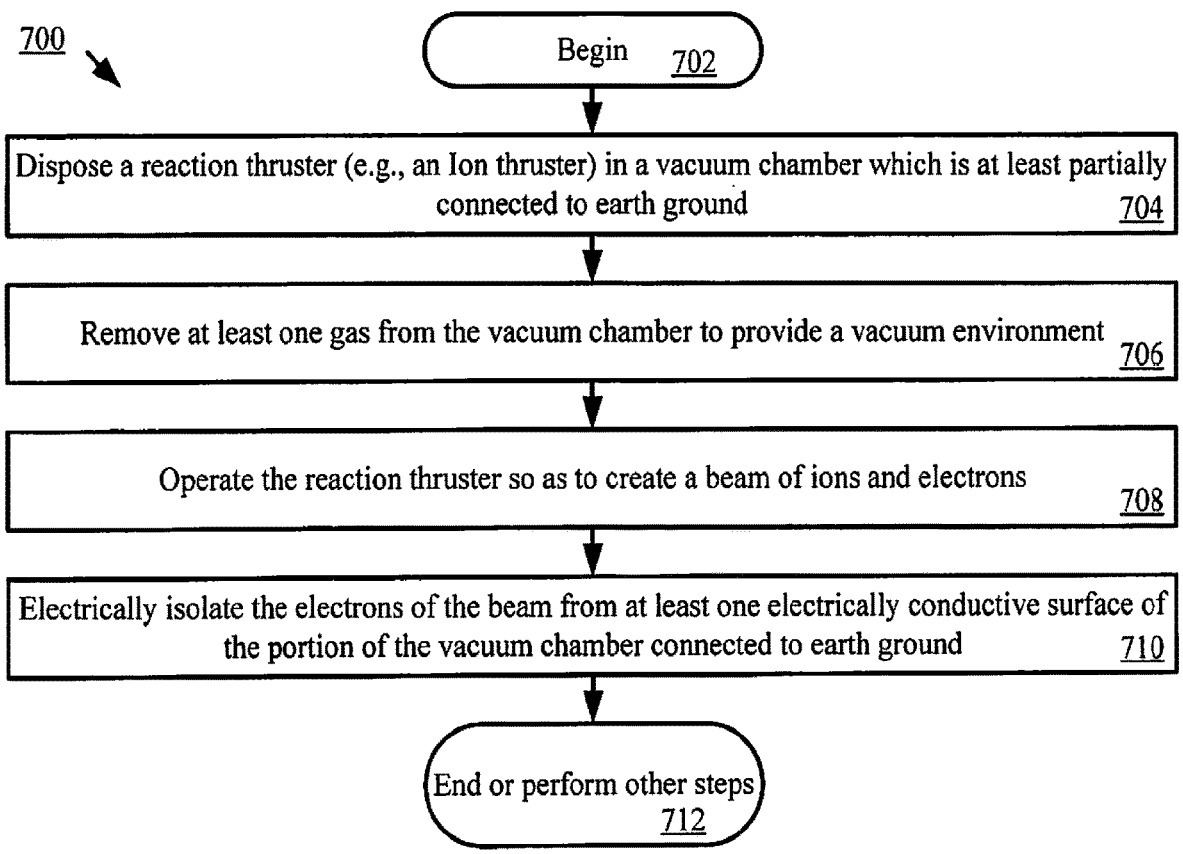
FIG. 7 is a flow diagram of an exemplary method for testing a reaction thruster in a test system.

Referring now to FIG. 7, there is provided a flow diagram of an exemplary method 700 for testing a reaction thruster (e.g., ion thruster 100 of FIG. 1). Method 700 begins with step 702 and continues with step 704. In step 704, the reaction thruster (e.g., ion thruster 100 of FIG. 1) is disposed in a vacuum chamber (e.g., vacuum chamber 302 of FIG. 3 or 402 of FIG. 4). The reaction thruster may comprise a floating ground. The vacuum chamber is at least partially connected to earth ground, and may optionally comprise a dielectric material disposed on at least one conductive internal surface thereof. Next in step 706, at least one gas is removed from the vacuum chamber to provide a vacuum environment. The vacuum environment may comprise a low density and pressure environment similar to a space environment. In this case, the pressure of gas within the vacuum chamber may be greater than, equal to or lower than $6 \times 10^{-6}$ Torr. Once the gas is removed from the vacuum chamber, the reaction thruster is operated so as to create a beam of ions and electrons, as shown by step 708.

Thereafter, step 710 is performed where the electrons of the beam are electrically isolated from at least one electrically conductive surface of the vacuum chamber. The electrical isolation can be achieved by applying an electrical bias voltage to the beam. The electrical bias voltage is applied to the beam using an electrode (e.g., electrode 350 of FIG. 1 or 450 of FIG. 4) disposed in and electrically isolated from the portion of the vacuum chamber connected to earth ground. In some scenarios, the electrode is a conductive object disposed within the vacuum chamber so as to be spaced apart from all adjacent vacuum chamber walls. The conductive object may be located in the vacuum chamber downstream from the reaction thruster. In other scenarios, the electrode comprises a first portion of at least one vacuum chamber wall which is electrically isolated from a grounded second portion of the vacuum chamber. The first portion of the vacuum chamber wall may be located at a downstream end of the vacuum chamber. In both cases, a voltage is applied to the electrode such that it has a more positive potential relative to the beam of ions and electrodes. The level of the voltage applied to the electrode may be constant throughout operation of the reaction thruster, or alternatively dynamically adjusted during operation of the reaction thruster. The dynamic adjustment may be based on at least one of a density of neutral gas within the vacuum chamber, a pressure of neutral gas within the vacuum chamber, a voltage of a cathode of the reaction thruster, a value of a current in plasma flowing from the reaction thruster, and an amount of current collected at the electrode. Upon competing step 710, step 712 is performed where method 700 ends or other steps are performed.

We claim:

1. A method for testing a reaction thruster in a terrestrial vacuum environment, comprising the steps of:
   disposing the reaction thruster in a vacuum chamber which is at least partially connected to earth ground and at least partially formed of a conductive material; and
   preventing electrons of a beam formed by the reaction thruster from being attracted to at least one electrically conductive surface of the vacuum chamber.

2. The method according to claim 1, wherein the preventing step comprises applying an electrical bias voltage to the beam.

3. The method according to claim 2, wherein the electrical bias voltage is applied to the beam using an electrode disposed inside and electrically isolated from the vacuum chamber.

4. The method according to claim 3, further comprising dynamically adjusting a level of a voltage applied to the electrode during operation of the reaction thruster.

5. The method according to claim 4, wherein the level is dynamically adjusted based on at least one of a density of neutral gas within the vacuum chamber, a voltage of a cathode of the reaction thruster to the vacuum chamber, a value of a current in plasma flowing from the reaction thruster, and an amount of current collected at the electrode.

6. The method according to claim 1, wherein the preventing step comprises applying a bias voltage to a downstream end or area of the vacuum chamber such that the downstream end or area has a more positive potential relative to the beam of ions and electrons.

7. The method according to claim 6, wherein the downstream end of the vacuum chamber is electrically isolated from an upstream end of the vacuum chamber which is connected to the earth ground.

8. The method according to claim 1, wherein the preventing step comprises disposing a dielectric material adjacent to the electrically conductive surface of the vacuum chamber.

9. The method according to claim 1, wherein the preventing step comprises disposing a floating material adjacent to the electrically conductive surface of the vacuum chamber.

10. The method according to claim 1, wherein the reaction thruster comprises a floating ground.

11. The method according to claim 1, further comprising electrically isolating the electrons or ions of the beam from at least one conductive surface of equipment disposed inside the vacuum chamber that is in electrical contact with the vacuum chamber.

12. A test system, comprising:
a vacuum chamber at least partially formed of a conductive material and comprising at least a first portion electrically connected to earth ground; and
an electrode configured to prevent electrons of a beam created by a reaction thruster from being attracted to at least one electrically conductive surface of the vacuum chamber.

13. The test system according to claim 12, wherein the electrons are prevented from being attracted to the electrically conductive surface by an application of an electrical bias voltage to the beam.

14. The test system according to claim 12, wherein the electrode is disposed inside and electrically isolated from the vacuum chamber.

15. The test system according to claim 14, further comprising a controller configured to facilitate a level adjustment of a voltage applied to the electrode during operation of the reaction thruster.

16. The test system according to claim 15, wherein the level is dynamically adjusted based on at least one of a density of neutral gas within the vacuum chamber, a voltage of a cathode of the reaction thruster to the vacuum chamber, a value of a current in plasma flowing from the reaction thruster, and an amount of current collected at the electrode.

17. The test system according to claim 11, wherein the electrode comprises at least a first portion of the vacuum chamber which has a more positive potential relative to the beam of ions and electrons.

18. The test system according to claim 17, wherein the first portion of the vacuum chamber is electrically isolated from a second portion of the vacuum chamber which is connected to ground.

19. The test system according to claim 11, further comprising a dielectric material disposed adjacent to the electrically conductive surface of the vacuum chamber.

20. The test system according to claim 11, further comprising a floating material disposed adjacent to the electrically conductive surface of the vacuum chamber.

* * * * *